(12) United States Patent
Horng et al.

(10) Patent No.: US 7,957,787 B2
(45) Date of Patent: *Jun. 7, 2011

(54) METHOD OF EXAMINING DYNAMIC CARDIAC ELECTROMAGNETIC ACTIVITY AND DETECTION OF CARDIAC FUNCTIONS USING RESULTS THEREOF

(76) Inventors: Herng-Er Horng, Taipei (TW);
Chau-Chung Wu, Taipei (TW);
Hong-Chang Yang, Taipei (TW);
Shieh-Yueh Yang, Taipei County (TW)

( * ) Notice: Subject to any disclaimer, the term of this patent is extended or adjusted under 35 U.S.C. 154(b) by 287 days.

This patent is subject to a terminal disclaimer.

(21) Appl. No.: 12/220,506

(22) Filed: Jul. 25, 2008

(65) Prior Publication Data

US 2009/0030301 A1    Jan. 29, 2009

Related U.S. Application Data

(63) Continuation-in-part of application No. 11/811,391, filed on Jun. 8, 2007.

(51) Int. Cl.
*A61B 5/05* (2006.01)
(52) U.S. Cl. ........................................ 600/409

(58) Field of Classification Search .................. 600/409
See application file for complete search history.

(56) References Cited

U.S. PATENT DOCUMENTS 6,115,628 A * 9/2000 Stadler et al. ................. 600/517

OTHER PUBLICATIONS

Wu et al.; "Two-dimensional propagations of megnetocardiac T wave signals for characterizing myocardial ischemia", Applied Physics Letters 92, 1 (2008), American Institute of Physics.

\* cited by examiner

*Primary Examiner* — Long V Le
*Assistant Examiner* — Michael T Rozanski
(74) *Attorney, Agent, or Firm* — J.C. Patents

(57) ABSTRACT

A method of examining cardiac electromagnetic activity over a heart for diagnosing the cardiac functions of the heart is disclosed. The method includes collecting a plurality of sets of spatially distributed, time-varying magnetic field signals of the heart of a subject, wherein the magnetic field signals exhibit features of at least a wave, identifying a time corresponding to a local maximum intensity of the magnetic field signals of the wave at each measurement position and plotting a temporal evolution of the local maximum intensity of the magnetic field signals during a time interval of the wave.

9 Claims, 4 Drawing Sheets
(2 of 4 Drawing Sheet(s) Filed in Color)

METHOD OF EXAMINING DYNAMIC CARDIAC ELECTROMAGNETIC ACTIVITY AND DETECTION OF CARDIAC FUNCTIONS USING RESULTS THEREOF

CROSS-REFERENCE TO RELATED APPLICATION

This application is a continuation-in-part of a prior application Ser. No. 11/811,391, filed on Jun. 8, 2007. The entirety of each of the above-mentioned patent applications is hereby incorporated by reference herein and made a part of specification.

BACKGROUND OF THE INVENTION

1. Field of Invention

The present invention relates to a method of examining dynamic cardiac electromagnetic activity and a detection of cardiac functions using the results thereof. More particularly, the present invention relates to a method of examining the magnetocardiographic signals and a diagnosis of coronary artery diseases using the results thereof.

2. Description of Related Art

Each heart beat is originated from the development a small pulse of electric current that spreads rapidly in the heart and causes the myocardium to contract (depolarization and repolarization). The electrical currents that are generated spread not only within the heart, but also throughout the body, resulting in the establishment of electric potentials on the body surface, which are detectable as changes in the electrical potential with an electrocardiograph (ECG). A typical ECG tracing of a normal heartbeat (or cardiac cycle) consists of a P wave, a PR interval, a QRS complex, a ST segment, a Q-T interval, a T wave and a U wave. In brief, the P wave represents the wave of depolarization that spreads from the SA node throughout the atria; the QRS complex corresponds to the depolarization of the ventricles; the T wave represents the repolarization (or recovery) of the ventricles; the U wave, which normally follows the T wave, is not always seen and is thought to represent the repolarization of the papillary muscles or Purkinje fibers. The Q-T interval represents the time for both ventricular depolarization and repolarization to occur; the ST segment following the QRS complex is the time at which the entire ventricle is depolarized. Any normal or abnormal deflections recorded by the ECG depend upon the origin of this chain of electrical activity. Hence, via the measurements of electrical activity during a cardiac cycle, cardiac functions or pathologies can be investigated.

Although electrocardiograph (ECG) provides information related to cardiac electrical activity, the ECG signals crucially depend on the contact between the electrodes and the body. Further, in order to obtain two-dimensional signals via ECG, many electrodes need to be placed on the body, which can be impractical and may create interference between signals. Moreover, to obtain more insightful results, it is often required to perform exercise electrocardiography test, which may impose discomfort to the patient. Therefore, alternative methods that are electrode-free, contact-free and stress-free are being investigated.

Non-contact measurement technologies, such as thallium scan, computer tomography, nuclear magnetic resonance imaging, etc. have been developed, as a diagnostic tool for coronary artery diseases (CAD). However, these methods require the participants to the injection of isotopes or contrast medium, or the subjection to X-ray or magnetic field, which is invasive, uncomfortable and potentially dangerous for the participants.

Many studies have demonstrated the benefit of magnetocardiography (MCG) imaging over the existing methods for certain clinical evaluation of cardiac functions and pathologies. Magnetocardiography is a noninvasive, contact-free, risk-free approach by measuring the magnetic fields of the heart generated by the same electric current as the ECG and will be altered where the electrical currents in the heart are disturbed. Although both MCG and ECG measure the cardiac depolarization and repolarization patterns, MCG may detect depolarization and repolarization in a different manner.

The magnetic signals of a beating heart can transmit through the body of a study subject and be sensed by sensors configured in proximity to but not in direct physical contact with the body. Hence, the problems in skin-electrode contact arising in ECG can be obviated. Further, MCG is less affected by the conductivity variations caused by other organs or tissues such as lung, bone and muscles. Many studies have demonstrated that MCG is potentially beneficial in various clinical applications.

However, one difficulty in obtaining the magnetocardiac signals is the weakness of the signals, which are in the order of tens of pico-Tesla for human. The superconducting quantum interference devices (SQUIDs), which exhibit a noise level less than the magnetocardiac signals by 2 to 3 orders in magnitude, have been developed to record magnetocardiac signals with an improved spatial-temporal signal resolution and a higher signal-to-noise ratio. Currently, there are many commercially available SQUID systems for detecting magnetocardiac signals. Some of these systems, which are known as multi-channel SQUID systems, may consist of many independent SQUID sensors (for example, more than 50 SQUID sensors) to allow the measurement of two-dimensional magnetocardiac signals originating from various sites over the heart. From a magnetocardiography, parameters such as α angles, smoothness index, current dipole moments can be estimated. Some reports have suggested that these parameters can be used as indicators for diagnosing cardiac functions or pathologies. However, other studies have indicated that these parameters overlap between normal and abnormal hearts. Hence, the existing MCG parameters are not adequate, in terms of sensitivity and specificity, for diagnosing cardiac functions or pathologies.

SUMMARY OF THE INVENTION

In view of the foregoing, the present invention provides a method of examining cardiac electromagnetic activity, wherein differentiation between a normally functioning and an abnormally functioning heart is enhanced.

The present invention also provides a method of examining cardiac electromagnetic activity, wherein localization of an injured myocardium can be achieved.

As embodied and broadly described herein, a method of examining cardiac electromagnetic activity according to a first embodiment of the invention includes constructing the wave propagation of electromagnetic signals of a heart. According to one aspect of the invention, sets of spatially distributed, time-dependent magnetic field data of the chest, corresponding to a plurality of measurement positions, are collected. A time corresponding to a local maximum (positive or negative) intensity of the magnetic field of a wave of the magnetic field data at each measurement position is then identified, followed by plotting a temporal evolution of the local maximum intensity of the magnetic field during a time interval of the wave.

According to one aspect of the invention, the magnetic signals are either two-dimensionally or three-dimensionally distributed over the heart.

According to one aspect of the present invention, each set of the spatially distributed, time-varying magnetic field data is offset.

According to one aspect of the present invention, each set of the spatially distributed, time-varying magnetic signals is representative of an intramyocardial, electrical behavior of the subject and comprises features of at least a P-wave, a Q-wave, a R-wave, a S-wave and a T-wave.

According to one aspect of the present invention, the offsetting is accomplished by zeroing an interval of each set of the spatially distributed, time-dependent magnetic field data before a P wave.

According to one aspect of the present invention, the temporal evolution the local maximum intensity of the magnetic field during a time interval of the T wave is plotted to obtain a propagation behavior of the T wave.

According to one aspect of the present invention, the temporal evolution of the local maximum intensity of the magnetic field during the time interval of the wave is characterized by a time-dependent area ratio of a positive wave area to a negative wave area.

According to one aspect of the present invention, the propagation behavior of a wave of a normally functioning heart and is different form that of an abnormally functioning heart.

According to one aspect of the present invention, the time-dependent area ratio starts from zero, then increases with time, and finally reaches a fixed value for a normal cardiac activity.

According to one aspect of the present invention, an abnormal cardiac activity shows a time-dependent area ratio peaks at least once at a certain time before the time-dependent area ratio reaches a fixed value.

In accordance to a method of examining cardiac electromagnetic activity of the present invention, the propagation behavior of a wave is useful in diagnosing coronary artery diseases and for localizing an ischemic part of the heart.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. The patent or application file contains at least one drawing executed in color. Copies of this patent or patent application publication with color drawing(s) will be provided by the Office upon request and payment of the necessary fee.

DESCRIPTION OF THE PREFERRED EMBODIMENTS

Measurements of MCG

A multichannel SQUID system, for example, a 64-channel SQUID system or other type of sensitive superconducting magnetometers, is positioned in a plurality of coordinates, for example in a two-dimension or three-dimensional array slightly above the thorax of a live specimen. Each sensor of the SQUID system registers the local extracorporeal magnet field strength as a function of time. A MCG system normally provides measurement of the magnetic field components perpendicular (z-component) ($B_z$) to the body surface as a function of time (t). Magnetocardiograph (MCG) has features similar to the P-wave, the QRS complex, the T-wave and the U-wave of the ECG (electrocardiography).

With the spatially distributed $B_z$-t curves, several diagnostic parameters such as a angles in MCG contour maps, smoothness index for the QT interval, etc. can be extracted. However, it has been identified that some patients having ischemia with values of these parameters not significantly different from those of normal individuals. Hence, relying on these conventional parameters may lead to erroneous diagnosis. Accordingly, the present invention provides a method of examining the electromagnetic activity, such as magnetocardiographic signals, wherein the differentiation between a normally functioning heart and an abnormally functioning heart is enhanced. Further, in accordance to the methods of examining the electromagnetic activity of the present invention, localization of the abnormality can be achieved.

Wave Propagation Method

The following disclosure is directed to an aspect of the present invention of examining cardiac electromagnetic activity. The method includes monitoring a wave propagation of magnetic signals, such as the magnetocardiographic signals.

Construction of Wave Propagation of MCG

The following is an exemplary illustration on how to construct a wave propagation from the spatially distributed $B_z$-t curves. In this embodiment, the T wave propagation is analyzed. However, it should be appreciated that these embodiments are presented by way of example and not by way of limitation, and the intent of the following detailed description is to cover all modifications, alternatives, and equivalents as may fall within the spirit and scope of the invention as defined by the appended claims. For example, the wave propagation of other interval or wave of the magnetocardiography signals may be examined.

Figure 1:
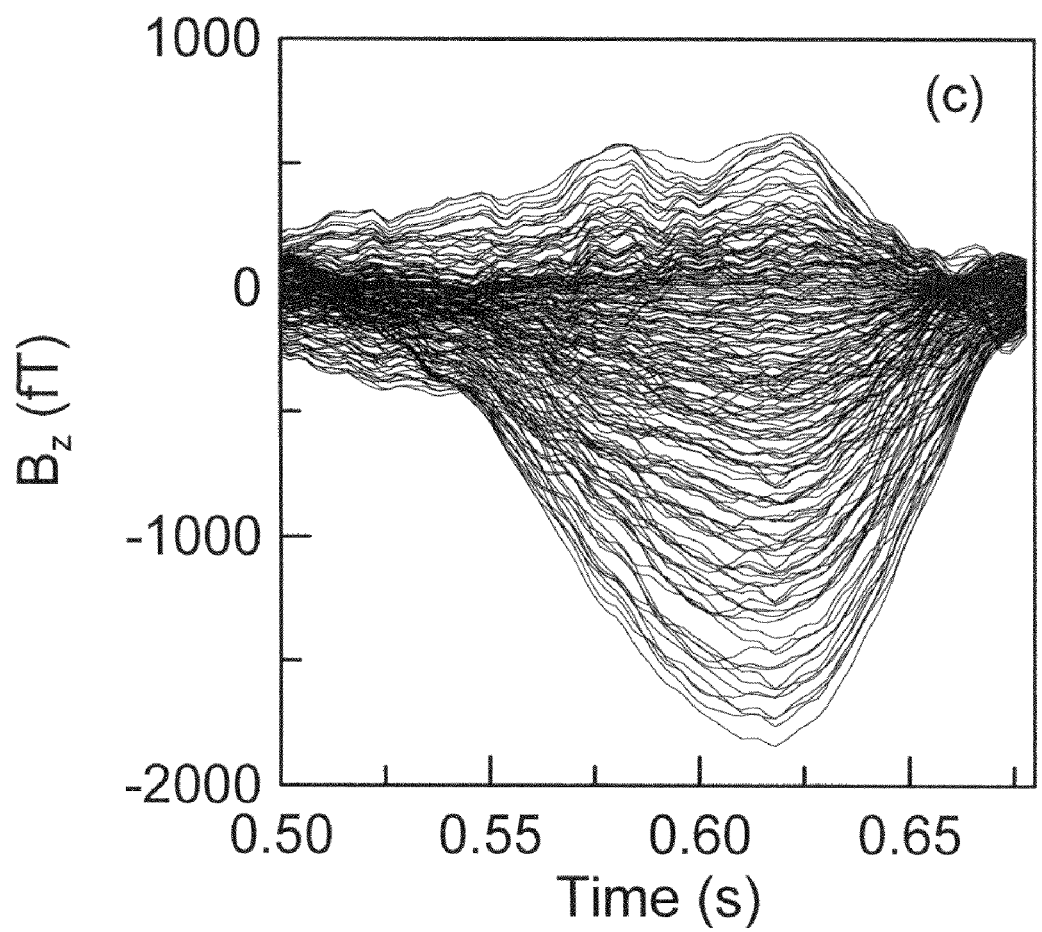
FIG. 1 is a magnified view of the T curve of a collection of $B_z$-t curves.
Figure 2:
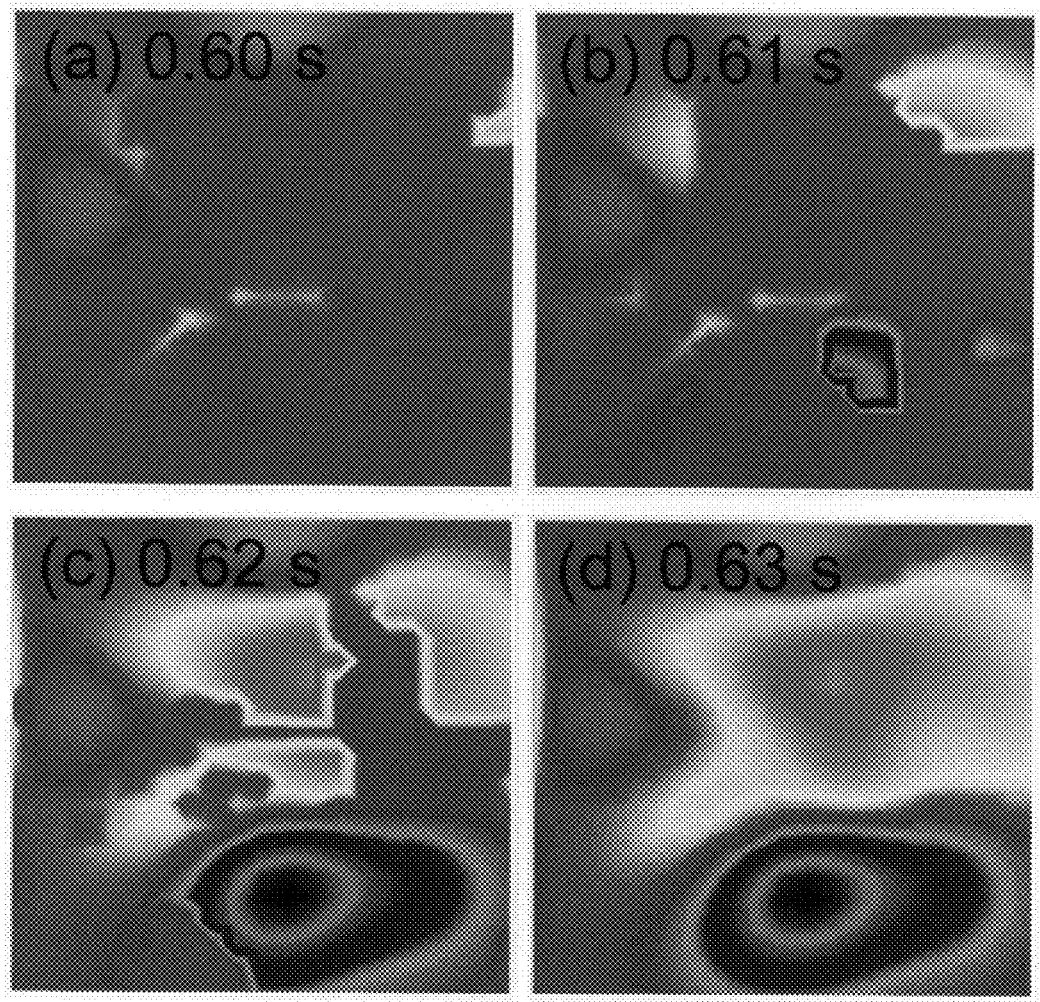
FIGS. 2(a) to 2(d) are color photographs showing a T-wave propagation of a normal heart.

Referring to FIG. 1, FIG. 1 is a magnified view of the collection of $B_z$-t curves at the T-wave interval. The maximum of each $B_z$-t curve at the T-wave interval occurs at different time points. Each $B_z$-t curve is usually referred as magnetocardiac signals sensed by an independent sensor channel or collected at a particular measurement position. The time corresponding to the positive/negative maximum $B_z$ of the N-th channel is defined as $t_{max,chN}$. As shown in FIG. 1, $t_{max,chN}$ of each channel varies in position in the x-y plane. As time progresses in a cardiac cycle, the positive/negative maximum $B_z$ of the N-th channel in the x-y plane at the time equal to $t_{max,chN}$ is determined. Hence, as time progresses through the T-wave interval, the two-dimensional propagation behavior of the T-wave over a heart is registered.

T-Wave Propagation of a Normal Heart Beat

MCG readings of 10 subjects without or with stenotic coronary artery of less than 50% of the luminal diameter identified by coronary angiography (CAG) are collected. After analyzing the T-wave propagation of each MCG, a typical behavior is identified, as shown in FIGS. 2(a) to 2(d). The yellow-to-red area refers to positive (+) T waves and the blue-to-black area refers to negative (−) T waves. Notably, the left/right side in FIGS. 2(a) to 2(d) represents the right/left side of the detected heart. To characterize the propagation of a T wave, the time-dependent area ratio of +T wave to −T wave is analyzed via the following equation (1), $$\text{Area ratio} \equiv \frac{A_{+T}(t)}{\text{constant} + A_{-T}(t)} \quad (1)$$

where $A_{+T}$ and $A_{-T}$ denote the area occupied by +T wave and −T wave respectively at a certain instant t. The constant in the denominator on the right side of Eq. (1) is artificially provided to avoid the area ratio becoming infinite whenever there is no −T wave. In this embodiment, the constant is set as 1. The typical time dependent area ratio for a normal heart is plotted in FIG. 3(a). The area ratio starts from zero, then gradually becomes larger, and finally reaches a saturated value. The behavior reveals with the curve in FIG. 3(a), in which the +T-wave area shows up more than the −T-wave area initially. Then, the +T-wave area increases almost at the same rate as the −T-wave area, and the +T-wave area increases to a plateau in the time-dependent area ratio in FIG. 3(a). This behavior coincides with those shown in FIG. 2.

T-Wave Propagation of an Abnormal Heart Beat

In addition to normal hearts, MCG's of 44 patients with stenotic (>50% of the luminal diameter) coronary artery disease (CAD) evidenced with coronary angiography (CAG) are also collected. The time-dependent area ratio of the T wave propagation is analyzed for each patient. A typical feature for the time-dependent area ratio is plotted with "square" symbols in FIG. 3(b). A clear peak occurs in the curve of the time-dependent area ratio at around 0.53 second. Physiologically, the +T wave should occur in sequence with time evolution along the myocardium over the heart. Thus, the area ratio is supposed to increase gradually with time, as observed in FIG. 3(a). The occurrence of the peak in the patients with stenotic coronary artery implies that +T waves at certain area of myocardium occur much earlier than that they are supposed to be if the myocardium was normal. The early occurrence of the +T waves can be attributed to the shorter action potential of ischemic myocardium. The stenotic coronary artery of the patient in FIG. 3(b) is then re-canalized with percutaneous coronary interventional (PCI) therapy. After the PCI procedure, the MCG is examined again and the time-dependent area ratio of T wave is analyzed, as shown with "cross" symbols in FIG. 3(b). The peak observed in the area ratio curve before the PCI procedure ("square" symbols) vanishes from the area ratio curve ("cross" symbols) after the PCI procedure. This observation suggests that the early occurrence of +T waves is eliminated through PCI therapy. Hence, the occurrence of the peak in the time-dependent area ratio of T wave promisingly acts as an indictor for identifying ischemia By using this criterion, i.e. with/without peaks in the time-dependent area ratio of T wave, the sensitivity and the specificity for screening myocardial ischemia is examined. The results are tabulated in Table 1. Table 1 summarizes the statistical results for diagnosing ischemia using time-dependent area ratio of T wave propagation detected with a SQUID-MCG system. The reference diagnosis is according to the diagnostic results via coronary angiography (CAG). The criterion for CAD in CAG is that the diameter stenosis of coronary artery is more than 50%. It is clear that 32 CAD patients can be identified from the 64 CAD patients via the method developed in this invention, which suggests that the sensitivity of the instant method is about 72.7% Furthermore, 9 persons are categorized as normal from 10 normal cases. Hence, the specificity is 90.0%.

TABLE 1

| MCG | CAG | |
|---|---|---|
| | CAD | NORMAL |
| CAD | 32 | 1 |
| NORMAL | 12 | 9 |

Since the occurrence of the peak in time-dependent area ratio shown in FIG. 3(b) is attributed to ischemic myocardium, the ischemic part can be localized by analyzing the T-wave propagation at times around the peak (~0.52 sec.). The T-wave propagation around 0.53 sec. is given in FIGS. 4(a) and 4(b). It is clear that the +T waves occur at around 0.53 sec are circled in FIG. 4(b). The circled area corresponds to ischemic part.

Figure 3:
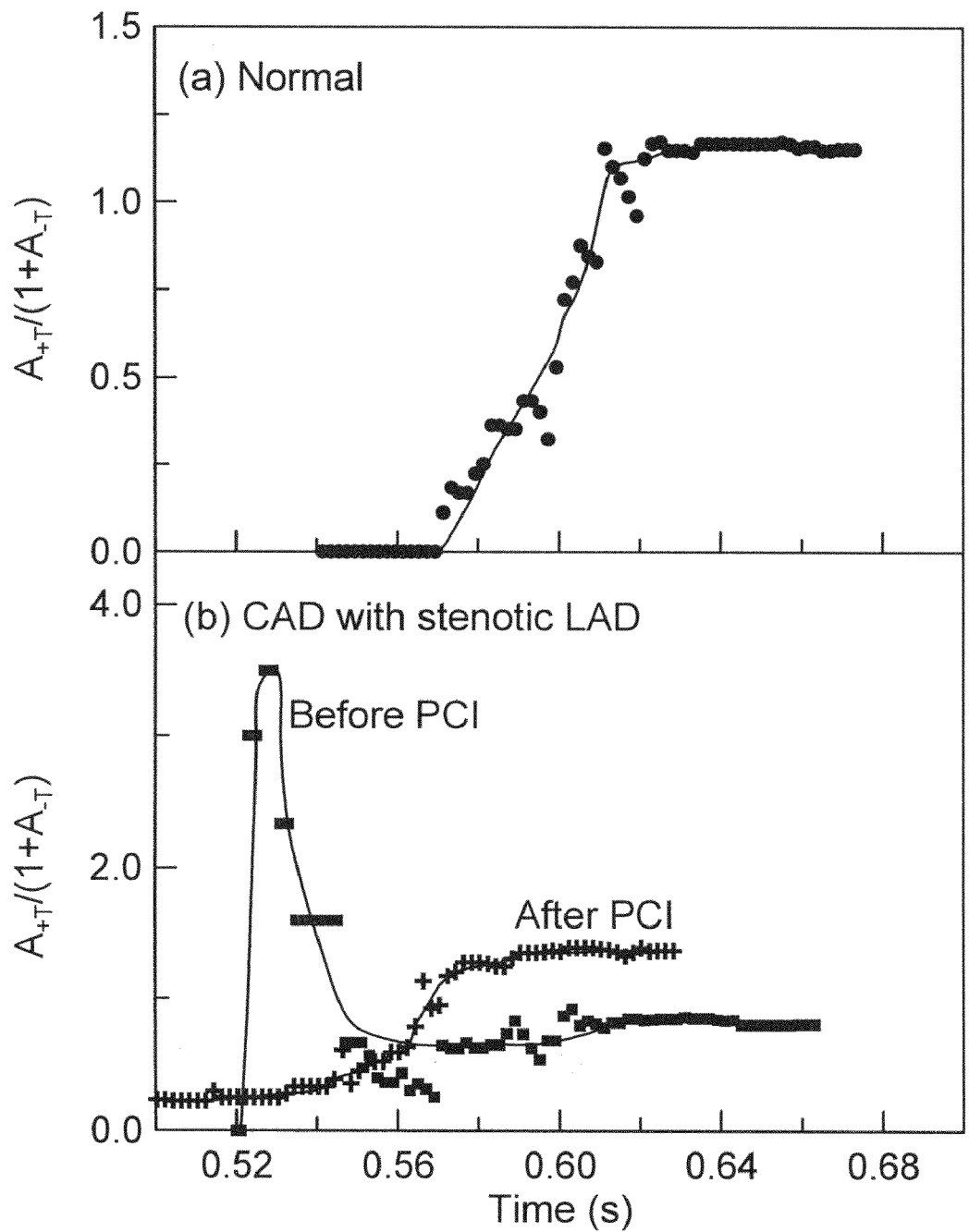
FIG. 3(a) is a diagram showing the time-dependent area ratio of +T-wave area to -T-wave area for a normal cardiac activity.
FIGS. 3(b) shows the time-dependent area ratio of the +T-wave area to the -T-wave area for an abnormal cardiac activity with stenotic left anterior descending (LAD) branch before percutaneous coronary interventions (PCI) and after PCT.
Figure 4:
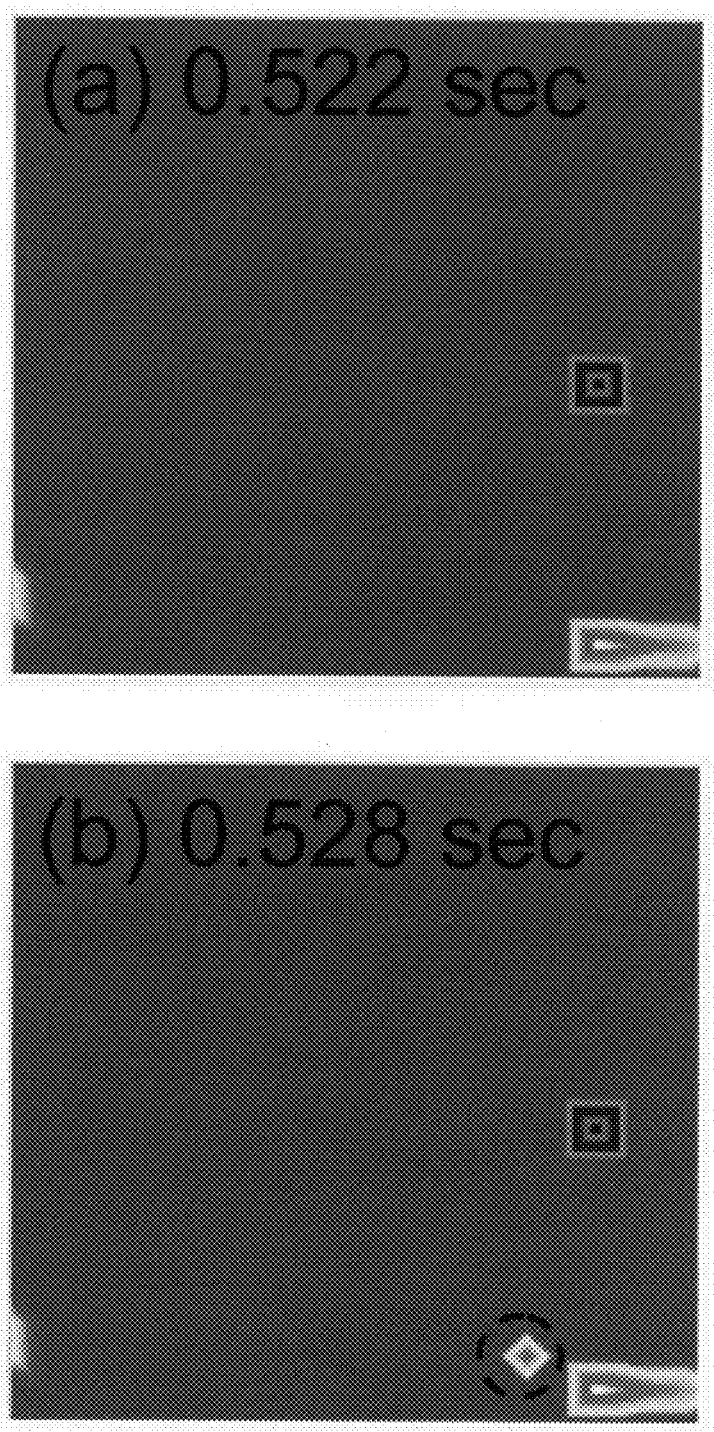
FIGS. 4(a) to 4(b) are color photographs showing a T-wave propagation of the abnormal heart showing the time-dependent area ratio in FIG. 3(b) before PCI at around 0.53 sec.

According to the results shown in FIGS. 3 and 4, it is apparent that the T-wave propagation of CAD patients is different from that of the normal population. Hence, via the examination on MCG T-wave propagation or other wave's propagation, an individual having CAD can be diagnosed. In addition, the present invention affords the possibility for localizing the abnormal regions, for example, ischemic regions, of the heart. The application of MCG wave propagation is not only useful for diagnostic purposes, it is also suitable for monitoring or following-up the effect of coronary intervention therapy, such as coronary artery bypass surgery, coronary angioplasty or stenting, and even after cardiac transplantation.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. A method of examining cardiac electromagnetic activity of a heart of a subject for diagnosing cardiac functions, the method comprising:

performing a non-contact magnetic measurement over a thorax region of the subject at a plurality of measurement positions to obtain a plurality of sets of spatially distributed, time-varying magnetic field signals of the heart of the subject, wherein each set of the spatially distributed, time-varying magnetic field signals at each of the measurement positions exhibits features of at least a wave;

offsetting each set of the time-varying magnetic field signals;

identifying a time ($t_{max,chN}$) corresponding to a local positive or negative maximum intensity of the each set of the offset time-varying magnetic field signals of the wave at the each of the measurement positions; and plotting a temporal evolution of the local maximum intensity of the offset time-varying magnetic field signals during a time interval of the wave to obtain a propagation behavior of the wave, wherein the temporal evolution of the local maximum intensity of the offset time-varying magnetic field signals during the time interval of the wave is characterized by a time-dependent area ratio of a positive wave area to a negative wave area.

2. The method of claim 1, wherein the each set of the time-varying magnetic field signals at the each of the measurement positions exhibits the features of at least a P-wave, a Q-wave, a R-wave, a S-wave, a T-wave or a combination thereof corresponding to that of an electrocardiography.

3. The method of claim 1, wherein the wave is a T-wave.

4. The method of claim 1, wherein the each set of the time-varying magnetic field signals is offset by zeroing an interval of the magnetic field signals before a P-wave.

5. The method of claim 1, wherein the time-varying magnetic field signals comprise magnetic field components perpendicular ($B_z$) to a surface of the subject.

6. The method of claim 1, wherein the time-dependent area ratio starts from zero, then increases with time, and finally reaches a fixed value for a normal cardiac activity.

7. The method of claim 1, wherein an abnormal cardiac activity shows the time-dependent area ratio peaks at least once at a certain time before the time-dependent area ratio reaches a fixed value.

8. The method of claim 1, wherein the propagation behavior of the wave is applicable in diagnosing coronary artery diseases.

9. The method of claim 1, wherein the propagation behavior of the wave is useful applicable in localizing ischemic regions of the heart.

* * * * *